United States Patent [19]

Roch et al.

[11] 4,260,621

[45] Apr. 7, 1981

[54] 3-AMINO-4-PHENYL-6-PIPERIDINO-1H-PYRAZOLO[3,4-B]-PYRIDINES AND SALTS THEREOF

[75] Inventors: Josef Roch; Erich Müller; Berthold Narr; Josef Nickl; Walter Haarmann, all of Biberach, Fed. Rep. of Germany

[73] Assignee: Boehringer Ingelheim GmbH, Ingelheim am Rhein, Fed. Rep. of Germany

[21] Appl. No.: 75,100

[22] Filed: Sep. 13, 1979

Related U.S. Application Data

[63] Continuation-in-part of Ser. No. 834,114, Sep. 19, 1977, Pat. No. 4,182,887.

[30] Foreign Application Priority Data

Sep. 29, 1976 [DE] Fed. Rep. of Germany ....... 2643753

[51] Int. Cl.³ .............................................. A61K 31/445
[52] U.S. Cl. .................................... 424/267; 424/256
[58] Field of Search ......................... 544/61; 546/119; 424/267, 263, 256

[56] References Cited

U.S. PATENT DOCUMENTS

| | | | |
|---|---|---|---|
| 3,872,133 | 3/1975 | Fleckenstein et al. | 546/119 X |
| 4,048,184 | 9/1977 | Hoehn | 546/119 OR |
| 4,182,887 | 1/1980 | Roch et al. | 546/119 |

Primary Examiner—John D. Randolph
Attorney, Agent, or Firm—Hammond, Littell, Weissenberger & Muserlian

[57] ABSTRACT

Compounds of the formula

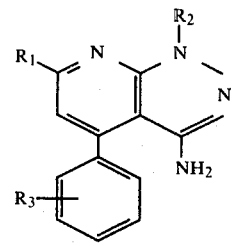

wherein
$R_1$ is unsubstituted, mono-substituted or di-substituted piperidino, where the substituents are selected from the group consisting of methyl, hydroxymethyl, hydroxyl, phenyl and benzyl;
$R_2$ is hydrogen, methyl or benzyl; and
$R_3$ is hydrogen, halogen, alkyl of 1 to 3 carbon atoms or alkoxy of 1 to 3 carbon atoms;

and non-toxic, pharmacologically acceptable acid addition salts thereof. The compounds as well as their salts are useful as antiphlogistics and antithrombotics.

2 Claims, No Drawings

3-AMINO-4-PHENYL-6-PIPERIDINO-1H-PYRAZOLO[3,4-B]-PYRIDINES AND SALTS THEREOF

This is a continuation-in-part of copending application Ser. No. 834,114, filed Sept. 19, 1977, now U.S. Pat. No. 4,182,887, issued Jan. 8, 1980.

This invention relates to novel 3-amino-4-phenyl-6-piperidino-1H-pyrazolo[3,4-b]pyridines and non-toxic acid addition salts thereof, as well as to a method of preparing these compounds.

More particularly, the present invention relates to a novel class of 1H-pyrazolo[3,4-b]pyridines represented by the formula

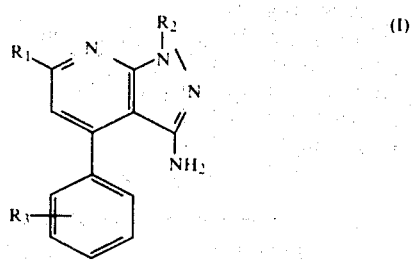

wherein
$R_1$ is unsubstituted, mono-substituted or di-substituted piperidino, where the substituents are selected from the group consisting of methyl, hydroxymethyl, hydroxyl, phenyl and benzyl;
$R_2$ is hydrogen, methyl or benzyl; and
$R_3$ is hydrogen, halogen, alkyl of 1 to 3 carbon atoms or alkoxy of 1 to 3 carbon atoms;
and non-toxic, pharmacologically acceptable acid addition salts thereof.

Specific embodiments of variable substitutes $R_1$, $R_2$ and $R_3$ are the following:
$R_1$—Piperidino, methyl-piperidino, dimethyl-piperidino, hydroxy-piperidino, hydroxymethyl-piperidino, phenyl-piperidino or benzyl-piperidino;
$R_2$—Hydrogen, methyl or benzyl;
$R_3$—Hydrogen, fluorine, chlorine, bromine, methyl, ethyl, propyl, methoxy, ethoxy or isopropoxy.

A preferred sub-genus thereunder is constituted by compounds of the formula I
where
$R_1$ is piperidino, methyl-piperidino, hydroxymethyl-piperidino, hydroxy-piperidino, phenyl-piperidino, benzyl-piperidino or dimethyl-piperidino;
$R_2$ is hydrogen, methyl or benzyl; and
$R_3$ is hydrogen, fluorine, chlorine, methyl or methoxy;
and non-toxic, pharmacologically acceptable acid addition salts thereof.

A further, especially preferred sub-genus thereunder is constituted by compounds of the formula I, where
$R_1$ is piperidino or 3-methyl-piperidino;
$R_2$ is hydrogen; and
$R_3$ is hydrogen, fluorine, chlorine, methyl or methoxy;
and non-toxic, pharmacologically acceptable acid addition salts thereof.

The compounds embraced by formula I may be prepared by reacting a 3-cyano-4-phenyl-pyridine of the formula

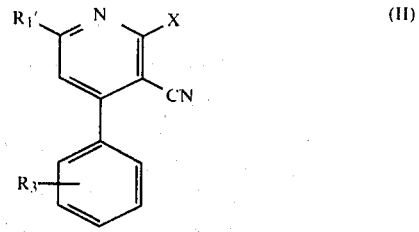

wherein
$R_3$ has the same meanings as in formula I;
$R_1'$ has the meanings defined for $R_1$ in formula I; and
X is a nucleophilically exchangeable, so-called leaving group, for example chlorine, bromine or aryloxy, such as phenoxy;
with a hydrazine of the formula

wherein $R_2$ has the same meanings as in formula I.

The reaction is advantageously carried out in the presence of a solvent such as dimethyl formamide, dimethyl sulfoxide, water, ethylene glycol, propylene glycol, 2-ethoxy-ethanol or in a stoichiometric excess of the hydrazine reactant of the formula III, optionally in the presence of a base such as sodium carbonate, pyridine or a sufficient excess of the hydrazine reactant, and at elevated temperatures, for instance at temperatures between 70° and 180° C., but preferably at temperatures between 100° and 150° C. The reaction may, however, also be carried out in the absence of a solvent.

The starting compounds of the formula II are also new, but may be prepared by known methods, for instance by reacting a corresponding 2,6-dihalo-3-cyano-4-phenyl-pyridine with an amine of the formula

wherein $R_1'$ has the same meanings as in formula II, in the presence of a solvent and at elevated temperatures, for example at the boiling point of a particular solvent which is used.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The following examples illustrate the present invention and will enable others skilled in the art to understand it more completely. It should be understood, however, that the invention is not limited solely to the particular examples given below. The melting points are uncorrected.

Preparation of starting compounds of the formula II:

EXAMPLE A 2,6-Dichloro-4-phenyl-3-cyano-pyridine (a) 84 gm (1 mol) of cyanoacetamide and 192 gm (1 mol) of ethyl benzoyl-acetate were dissolved in 200 ml of absolute ethanol while heating. While continuing to heat the resulting solution, a solution of 56 gm (1 mol) of potassium hydroxide in 200 ml of absolute ethanol was added dropwise thereto over a period of about two hours. Thereafter, the resulting mixture was refluxed for about 20 hours, during which time the potassium salt of 2,6-dihydroxy-4-phenyl-3-cyano-pyridine precipitated out. After allowing the mixture to cool, the precipitate was collected by suction filtration and dissolved in 2 to 3 liters of hot water, and the hot aqueous solution was acidified with concentrated hydrochloric acid, whereupon ivory-colored crystals separated out. After cooling, the crystals were collected by suction filtration, washed with water and a small amount of acetone and dried, yielding 89 gm (42% of theory) of 2,6-dihydroxy-4-phenyl-3-cyano-pyridine, m.p. about 280° C. (decomp.)

(b) A mixture consisting of 42.4 gm (0.2 mol) of 2,6-dihydroxy-4-phenyl-3-cyano-pyridine and 300 ml of phosphorus oxychloride was heated for 6 hours at about 180° C. in a pressure vessel made of glass, while shaking the vessel. Thereafter, the reaction mixture was allowed to cool and was then added in small portions to a mixture of ice and water (about 3 liters), while stirring. The precipitate formed thereby was collected by suction filtration, washed with water and dried, yielding 47.4 gm (95% of theory) of the raw reaction product. The raw product was dissolved in chloroform (the small amount of insoluble matter was filtered off) and purified by passing the solution through a short silicagel column with chloroform as the flow agent. The combined chloroform fractions were evaporated, leaving as a residue 37.5 gm (75% of theory) of virtually colorless crystalline 2,6-dichloro-4-phenyl-3-cyano-pyridine of the formula

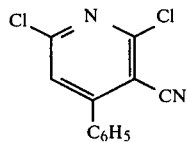

which had a melting point of 167°-169° C.

EXAMPLE B

Using a procedure analogous to that described in Example A (b), except that the reaction was carried out at atmospheric pressure, 2,6-dibromo-4-phenyl-3-cyano-pyridine, m.p. 186°-188° C. (recrystallized from ethyl acetate), was prepared by reacting 2,6-dihydroxy-4-phenyl-3-cyano-pyridine with phosphorus oxybromide or with phosphorus tribromide and triethylamine.

EXAMPLE C

2-Chloro-6-morpholino-4-phenyl-3-cyano-pyridine

A suspension of 24.9 gm (0.1 mol) of 2,6-dichloro-4-phenyl-3-cyano-pyridine in 400 ml of ethanol was slowly admixed with 17.4 gm (0.2 mol) of morpholine, and the resulting mixture was refluxed for about two hours. Even while refluxing, but primarily upon subsequent cooling (optionally on an ice water bath) of the reaction mixture, a colorless crystalline precipitate formed which was collected by suction filtration, very thoroughly washed with water and dried. 25.8 gm (86% of theory) of 2-chloro-6-morpholino-4-phenyl-3-cyanopyridine, m.p. 198°-200° C., were obtained.

Using a procedure analogous to that described in Example C, the following starting compounds of the formula II were also prepared.
2-Chloro-4-phenyl-6-piperidino-3-cyano-pyridine, m.p.: 173°-176° C.
2-Chloro-6-(2-methyl-piperidino)-4-phenyl-3-cyano-pyridine, m.p.: 103°-106° C.
2-Chloro-6-(3-methyl-piperidino)-4-phenyl-3-cyano-pyridine, m.p.: 108°-110° C.
2-Chloro-6-(4-methyl-piperidino)-4-phenyl-3-cyano-pyridine, m.p.: 130°-132° C.
2-Chloro-6-(2,6-dimethyl-piperidino)-4-phenyl-3-cyano-pyridine, m.p.: 120°-123° C.
6-(4-Benzyl-piperidino)-2-chloro-4-phenyl-3-cyano-pyridine, m.p.: 141°-143° C.
2-Chloro-4-phenyl-6-(4-phenyl-piperidino)-3-cyano-pyridine, m.p.: 183°-185° C.
2-Chloro-6-(3-hydroxymethyl-piperidino)-4-phenyl-3-cyanopyridine, m.p.: 150°-153° C.
2-Chloro-6-(3-hydroxy-piperidino)-4-phenyl-3-cyano-pyridine, m.p.: 183°-185° C.

Preparation of end products of the formula I:

EXAMPLE 1

3-Amino-6-morpholino-4-phenyl-1H-pyrazolo[3,4-6]pyridine and its hydrochloride

A mixture consisting of 15.0 gm (0.05 mol) of 2-chloro-6-morpholino-4-phenyl-3-cyano-pyridine (see Example C), 20 ml of 80% hydrazine hydrate and 100 ml of ethylene glycol was heated for 3 hours at 130° C. Thereafter, the resulting solution was poured into about 1 liter of water, whereupon a virtually colorless precipitate formed which was collected by suction filtration, washed with water and then immediately reprecipitated from 700 ml of 0.1 N hydrochloric acid with concentrated ammonia. The reprecipitated product was collected by suction filtration, washed and dried, yielding 13.7 gm (93% of theory) of practically pure 3-amino-6-morpholino-4-phenyl-1H-pyrazolo[3,4-b]pyridine, m.p. 178°-180° C., of the formula

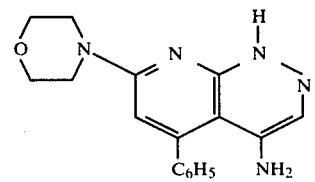

After recrystallization from ethanol it had a melting point of 180°-182° C.

| Elemental analysis $C_{16}H_{17}N_5O$: mol. wt. 295.3 | | |
| --- | --- | --- |
| Calculated: C-65.07%; | H-5.80%; | N-23.71% |
| Found: C-65.20%; | H-6.10% | N-23.80% |

The hydrochloride of 3-amino-6-morpholino-4-phenyl-1H-pyrazolo[3,4-b]pyridine, m.p. 263°-265° C., was obtained by dissolving the free based in about 2 N hydrochloric acid while heating, and letting the salt crystallize out.

EXAMPLE 2

3-Amino-6-(2-methyl-piperidino)-4-phenyl-1H-pyrazolo[3,4-b]pyridine, m.p. 163°-165° C., was prepared analogous to Example 1 from 2-chloro-6-(2-methyl-piperidino)-4-phenyl-3-cyano-pyridine (m.p. 103°–106° C.) and hydrazine hydrate.

EXAMPLE 3

3-Amino-6-(3-methyl-piperidino)-4-phenyl-1H-pyrazolo[3,4-b]-pyridine, m.p. 182°–185° C., was prepared analogous to Example 1 from 2-chloro-6-(3-methyl-piperidino)-4-phenyl-3-cyano-pyridine (m.p. 108°–110° C.) and hydrazine hydrate in propylene glycol.

EXAMPLE 4

3-Amino-6-(4-methyl-piperidino)-4-phenyl-1H-pyrazolo[3,4-b]pyridine, m.p. 206°–208° C., was prepared analogous to Example 1 from 2-chloro-6-(4-methyl-piperidino)-4-phenyl-3-cyano-pyridine (m.p. 130°–132° C.) and hydrazine hydrate.

EXAMPLE 5

3-Amino-6-(2,6-dimethyl-piperidino)-4-phenyl-1H-pyrazolo of [3,4-b]-pyridine, m.p. 210°–212° C., was prepared analogous to Example 1 from 2-chloro-6-(2,6-dimethyl-piperidino)-4-phenyl-3-cyano-pyridine (m.p. 120°–123° C.) and hydrazine hydrate.

EXAMPLE 6

3-Amino-6-(4-benzyl-piperidino)-4-phenyl-1H-pyrazolo[3,4-b]pyridine, m.p. 182°–185° C. (from ethyl acetate), was prepared analogous to Example 1 from 6-(4-benzyl-piperidino)-2-chloro-4-phenyl-3-cyano-pyridine (m.p. 141°–143° C.) and hydrazine hydrate.

EXAMPLE 7

3-Amino-4-phenyl-6-(4-phenyl-piperidino)-1H-pyrazolo[3,4-b]pyridine, m.p. 225°–228° C., was prepared analogous to Example 1 from 2-chloro-4-phenyl-6-(4-phenyl-piperidino)-3-cyano-pyridine (m.p. 183°–185° C.) and hydrazine hydrate.

EXAMPLE 8

3-Amino-6-(3-hydroxymethyl-piperidino)-4-phenyl-1H-pyrazolo[3,4-b]-pyridine, m.p. 210°–212° C., was prepared analogous to Example 1 from 2-chloro-6-(3-hydroxymethyl-piperidino)-4-phenyl-3-cyano-pyridine (m.p. 150°–153° C.) and hydrazine hydrate.

EXAMPLE 8a

3-Amino-4-phenyl-6-piperidino-1H-pyrazolo[3,4-b]pyridine, m.p. 196°–199° C., was prepared analogous to Example 1 from 2-chloro-4-phenyl-6-piperidino-3-cyano-pyridine (m.p. 173°–176° C.) and hydrazine hydrate.

EXAMPLE 9

3-Amino-6-(3-hydroxy-piperidino)-4-phenyl-1H-pyrazolo[3,4-b]-pyridine, m.p. 225°–227° C., was prepared analogous to Example 1 from 2-chloro-6-(3-hydroxy-piperidino)-4-phenyl-3-cyanopyridine (m.p. 183°–185° C.) and hydrazine hydrate.

EXAMPLE 10

3-Amino-4-(4-methoxy-phenyl)-6-piperidino-1H-pyrazolo[3,4-b]pyridine, m.p. 211°–213° C., was prepared analogous to Example 1 from 2-chloro-4-(4-methoxy-phenyl)-6-piperidino-3-cyanopyridine (m.p. 189°–190° C.) and hydrazine hydrate.

The compounds of the present invention, that is, those embraced by formula I above and their non-toxic, pharmacologically acceptable acid addition salts, have useful pharmacodynamic properties. More particularly, they exhibit antithrombotic and antiphlogistic activities in warm-blooded animals such as mice.

Certain 3-amino-1H-pyrazolo[3,4-b]pyridines are disclosed in the prior art, namely in German Offenlegungsschrift No. 2,232,038, but the utility ascribed to them is that of intermediates for the preparation of dyes, especially of azodyes.

The antithrombotic properties of the compounds of the present invention were ascertained by the standard test method described below, and Table I shows the test results for a few representative species, where A = 3-Amino-4-phenyl-6-piperidino-1H-pyrazolo[3,4-b]pyridine B = 3-Amino-6-(3-methyl-piperidino)-4-phenyl-1H-pyrazolo[3,4-b]pyridine, C = 3-Amino-4-(4'-methoxy-phenyl)-6-piperidino-1H-pyrazolo-[3,4-b]pyridine, and D = 3,6-Diamino-4-phenyl-1H-pyrazolo[3,4-b]pyridine, disclosed in German Offenlegungsschrift No. 2,232,038.

1. Determination of effect on platelet aggregation by the method of Born and Cross, J. Physiol. 170, 397 (1964):

The thrombocyte aggregation was measured in the platelet-rich plasma of healthy human donors. The course of change of the optical density of the platelet suspension was measured and recorded photometrically after the addition of commercial collagen containing 1 mg of collagen fibrils per ml. From the angle of inclination of the density curve, the rate of aggregation was estimated (Vmas). The optical density (O.D.) was taken as the point on the curve where the most light was transmitted.

As small doses of collagen as possible were chosen, but sufficient to give irreversible aggregation. To provoke maximum aggregation, about 0.01 ml of the collagen solution was added to 1 ml of platelet-rich plasma.

The test compounds were incubated at 37° C. for 10 minutes with the plasma before aggregation was provoked. The compounds were dissolved with a small quantity of hydrochloric acid or dimethyl formamide, and the solution was diluted to the desired final concentration with distilled water.

The dose leading to a 50% inhibition of aggregation compared with the control group ($ED_{50}$) was determined.

TABLE I

| Compound | $ED_{50}$ μmol/liter |
| --- | --- |
| A | 0.4 |
| B | 0.3 |
| C | 1 |
| D | 100 |

2. Acute toxicity:

The acute toxicity of the compounds was determined in white mice (observation time: 14 days) after oral administration of a single dose:

TABLE II

| Compounds | Acute Toxicity |
| --- | --- |
| A | > 250 mgm/kg (0 out of 10 animals died) |
| B | > 250 mgm/kg (0 out of 10 animals died) |
| C | >1,500 mgm/kg (0 out of 10 animals died) |
| D | >1,500 mgm/kg (0 out of 10 animals died) |

Thus, the compounds of the present invention are useful for the prophylactic and therapeutic treatment of arterial thromboembolisms and arterial occlusion disorders.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 3.34 mgm/kg body weight, preferably from 2.0 to 2.84 mgm/kg body weight.

The following examples illustrate a few pharmaceutical dosage unit compositions comprising a compound of the present invention as an active ingredient and represent the best modes contemplated of putting the invention into practical use. The parts are parts by weight, unless otherwise specified.

EXAMPLE 11

Tablets

The tablet composition is compounded from the following ingredients:

| | | |
|---|---|---|
| 3-Amino-6-piperidino-4-phenyl-1H-pyrazolo[3,4-b]pyridine | | 150.0 parts |
| Lactose | | 218.0 parts |
| Potato starch | | 86.0 parts |
| Polyvinylpyrrolidone | | 11.0 parts |
| Magnesium stearate | | 5.0 parts |
| | Total | 470.0 parts |

Preparation:

The active ingredient is intimately admixed with the lactose and the potato starch, the mixture is uniformly moistened with an ethanolic 20% solution of the polyvinylpyrrolidone, and the moist mass is granulated through a 2.0 mm-mesh screen. The granulate is dried at 45° C., passed through a 1.5 mm-mesh screen and admixed with the magnesium stearate, and the composition is compressed into 470 mgm-tablets in a conventional tablet press. Each tablet is an oral dosage unit composition containing 150 mgm of the active ingredient.

EXAMPLE 12

Coated pills

The pill core composition is compounded from the following ingredients:

| | | |
|---|---|---|
| 3-Amino-6-piperidino-4-phenyl-1H-pyrazolo[3,4-b]pyridine | | 100.0 parts |
| Lactose | | 150.0 parts |
| Corn starch | | 60.0 parts |
| Polyvinylpyrrolidone | | 7.0 parts |
| Magnesium stearate | | 3.0 parts |
| | Total | 320.0 parts |

Preparation:

The ingredients are compounded in the usual manner as in the preceding example, and the composition is compressed into 320 mgm-pill cores which are subsequently coated with a thin shell consisting essentially of a mixture of sugar and talcum and finally polished with beeswax. Each coated pill is an oral dosage unit composition containing 100 mgm of the active ingredient.

EXAMPLE 13

Hypodermic solution

The solution is compounded from the following ingredients:

| | |
|---|---|
| 3-Amino-6-piperidino-4-phenyl-hydrochloride 1H-pyrazolo[3,4-b]pyridine- | 100.0 parts |
| Polyethylene glycol 600 | 200.0 parts |
| Distilled water q.s. ad | 5000.0 parts by vol. |

Preparation:

Distilled water is pretreated by boiling it and then cooling it to room temperature in an atmosphere of nitrogen. The polyethylene glycol and the active ingredient are then dissolved in the pretreated distilled water in an atmosphere of nitrogen, and the solution is diluted to the indicated volume with additional pretreated distilled water and then filtered until free from suspended particles. The filtrate is filled into brown 5 cc-ampules in an atmosphere of nitrogen, which are then sterilized for 20 minutes at 121° C. and sealed. The entire procedure must be carried out in diffused light. The contents of each ampule are an injectable dosage unit composition containing 100 mgm of the active ingredient.

EXAMPLE 14

Drop solution

The solution is compounded from the following ingredients:

| | |
|---|---|
| 3-amino-6-piperidino-4-phenyl-1H-pyrazolo[3,4-b]pyridine hydrochloride | 50.0 parts |
| Cane sugar | 350.0 parts |
| Sorbic acid | 1.0 parts |
| Essence of cacao | 50.0 parts |
| Ethanol | 200.0 parts by vol. |
| Polyethylene glycol 600 | 100.0 parts by vol. |
| Distilled water q.s. ad | 1000.0 parts by vol. |

Preparation:

The sorbic acid is dissolved in the ethanol, an equal volume of distilled water is added thereto, and the active ingredient is dissolved in the solution (solution I). The sugar is dissolved in the remaining distilled water (solution II). Solution II, the polyethylene glycol and the essence of cacao are added to solution I while stirring, and the resulting solution is filtered. The entire procedure must be carried out in an atmosphere of nitrogen, and the finished solution must be bottled and stored under these conditions. 1 ml of the filtrate (about 20 drops) is an oral dosage unit composition containing 50 mgm of the active ingredient.

EXAMPLE 15

Suppositories

The suppository composition is compounded from the following ingredients:

| | |
|---|---:|
| 3-Amino-6-piperidino-4-phenyl-1H-pyrazolo[3,4-b]pyridine | 200.0 parts |
| Suppository base (e.g. cocoa butter) | 1500.0 parts |
| Total | 1700.0 parts |

Preparation:

The finely pulverized active ingredient is homogeneously blended with an immersion homogenizer into the suppository base which had previously been melted and cooled to 40° C. 1700 mgm-portions of the mixture are poured at 38° C. into cooled suppository molds and allowed to harden therein. Each suppository is a rectal dosage unit composition containing 200 mgm of the active ingredient.

Any one of the other compounds embraced by formula I or a non-toxic pharmacologically acceptable acid addition salt thereof may be substituted for the particular active ingredient in Examples 11 through 15. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An antithrombotic pharmaceutical dosage unit composition consisting essentially of an inert pharmaceutical carrier and an effective antithrombotic amount of a compound of the formula

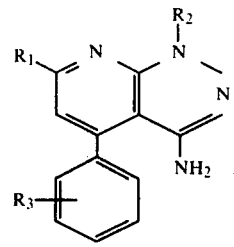

wherein
$R_1$ is unsubstituted, mono-substituted or di-substituted piperidino, where the substituents are selected from the group consisting of methyl, hydroxymethyl, hydroxyl, phenyl and benzyl;
$R_2$ is hydrogen, methyl or benzyl; and
$R_3$ is hydrogen, halogen, alkyl of 1 to 3 carbon atoms or alkoxy of 1 to 3 carbon atoms;
or a non-toxic, pharmacologically acceptable acid addition salt thereof.

2. The method of preventing or relieving thrombosis in a warm-blooded animal in need thereof, which comprises perorally, parenterally or rectally administering to said animal an effective antithrombotic amount of a compound of the formula

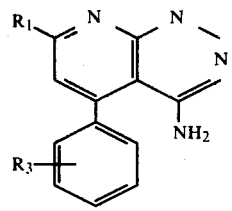

wherein
$R_1$ is unsubstituted, mono-substituted or di-substituted piperidino, where the substituents are selected from the group consisting of methyl, hydroxymethyl, hydroxyl, phenyl and benzyl;
$R_2$ is hydrogen, methyl or benzyl; and
$R_3$ is hydrogen, halogen, alkyl of 1 to 3 carbon atoms or alkoxy of 1 to 3 carbon atoms;
or a non-toxic, pharmacologically acceptable acid addition salt thereof.

* * * * *

UNITED STATES PATENT AND TRADEMARK OFFICE
CERTIFICATE OF CORRECTION

PATENT NO. : 4,260,621
DATED      : April 7, 1981
INVENTOR(S) : JOSEF ROCH ET AL.

It is certified that error appears in the above—identified patent and that said Letters Patent is hereby corrected as shown below:

Column 4, line 25: "[3,4-" should read -- [3,4-6]-
         line 26: Delete "6]"

Column 4: The portion of the structural formula which reads

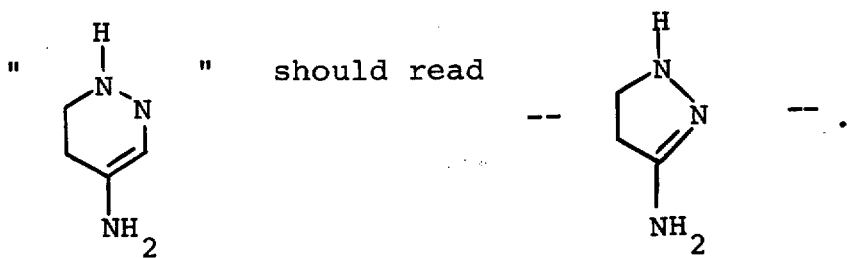

Column 5, line 48; Column 6, line 14:"[3,4-" should read -- [3,4-b]- --.

Column 5, line 49; Column 6, line 15: Delete "b]".

Signed and Sealed this

Fourteenth Day of July 1981

[SEAL]

Attest:

GERALD J. MOSSINGHOFF

Attesting Officer    Commissioner of Patents and Trademarks